United States Patent [19]
Matz

[11] Patent Number: 5,586,562
[45] Date of Patent: Dec. 24, 1996

[54] DEVICE FOR SENSING AND TREATING BRUXISM

[76] Inventor: Warren W. Matz, 882 U.S. Highway 1, Juno Beach, Fla. 33408

[21] Appl. No.: 502,681

[22] Filed: Jul. 14, 1995

[51] Int. Cl.$^6$ ..................................... A61F 5/56
[52] U.S. Cl. ........................... 128/848; 128/859
[58] Field of Search ............ 128/848, 859–862; 2/2

[56] References Cited

U.S. PATENT DOCUMENTS

| | | | |
|---|---|---|---|
| 4,169,473 | 10/1979 | Samelson | 128/848 |
| 4,304,227 | 12/1981 | Samelson . | |
| 4,934,378 | 6/1990 | Perry, Jr. . | |
| 5,117,816 | 6/1992 | Shapiro | 128/200.24 |
| 5,190,051 | 3/1993 | Wilson | 128/777 |
| 5,265,624 | 11/1993 | Bowman | 128/848 |
| 5,277,203 | 1/1994 | Hays . | |
| 5,284,161 | 2/1994 | Karell | 128/848 |

*Primary Examiner*—Michael A. Brown
*Attorney, Agent, or Firm*—McHale & Slavin, P.A.

[57] ABSTRACT

The instant invention is a device and method for treatment of bruxism, snoring, and sleep apnea based upon an inconspicuously placed tooth guard which, in the preferred embodiment, includes a pressure sensitive surface which is electrically coupled to an alarm mechanism. The alarm mechanism is activated when the contact area is compressed and may be constructed of sensitive materials so as to detect vibrations indicative of snoring. The device attaches to release clips bonded to the side of a tooth with a sensing area positioned between the teeth so as to indicate bruxism is occurring. The alarm mechanism will provide a resonant frequency capable of making a sound or providing a vibration indicating to the individual that bruxism is occurring. A timer mechanism can be used to delay operation of the alarm. Alternatively, the timer mechanism can be made operational wherein the lack of circuit contact will cause alarm so as to indicated sleep apnea. An alternative embodiment of the invention provides a tooth guard as part of the bruxism treatment wherein once the alarm mechanism has broken the habit of bruxism, the guard reinforces antibruxism without the alarm function.

17 Claims, 3 Drawing Sheets

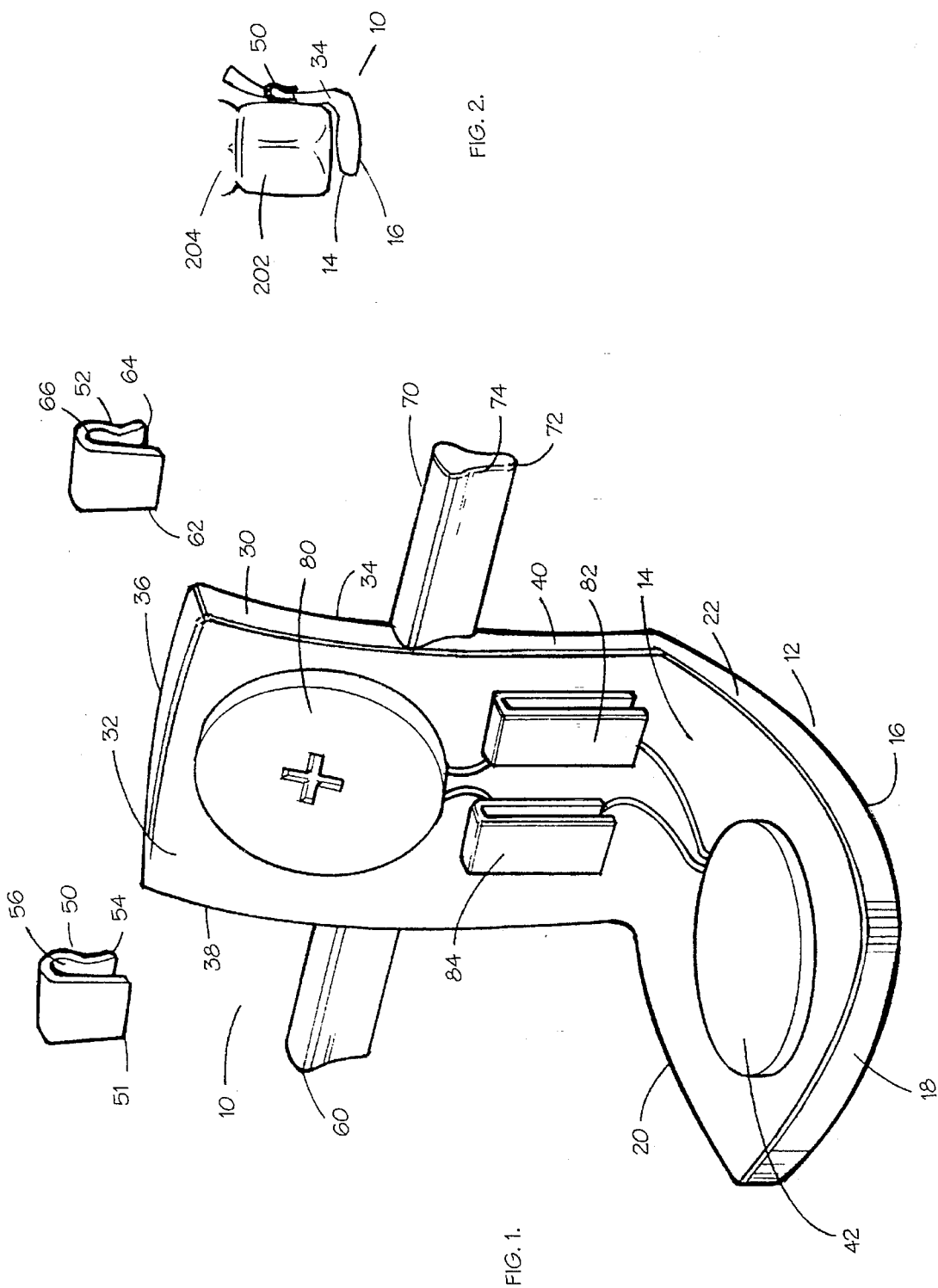

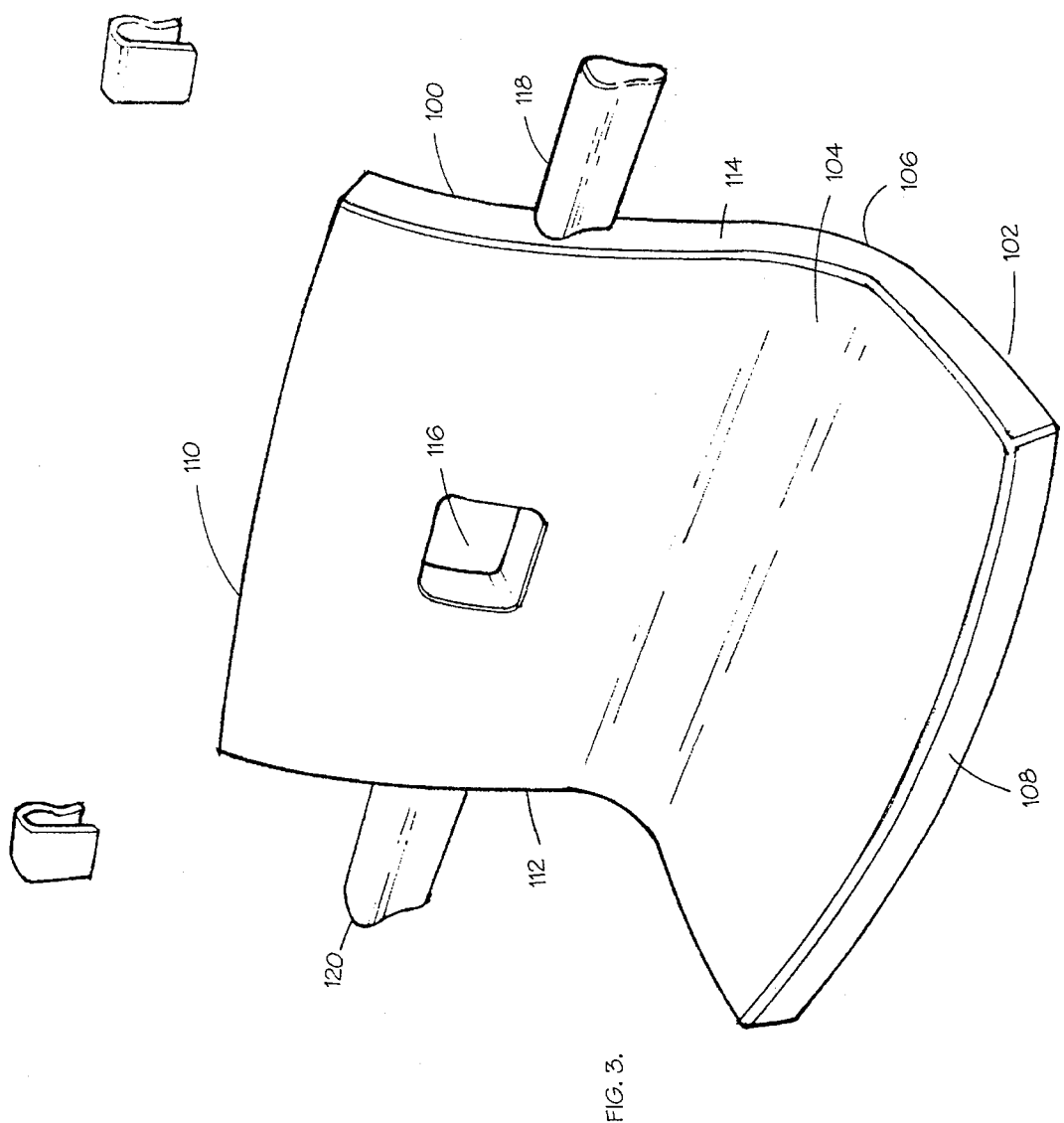

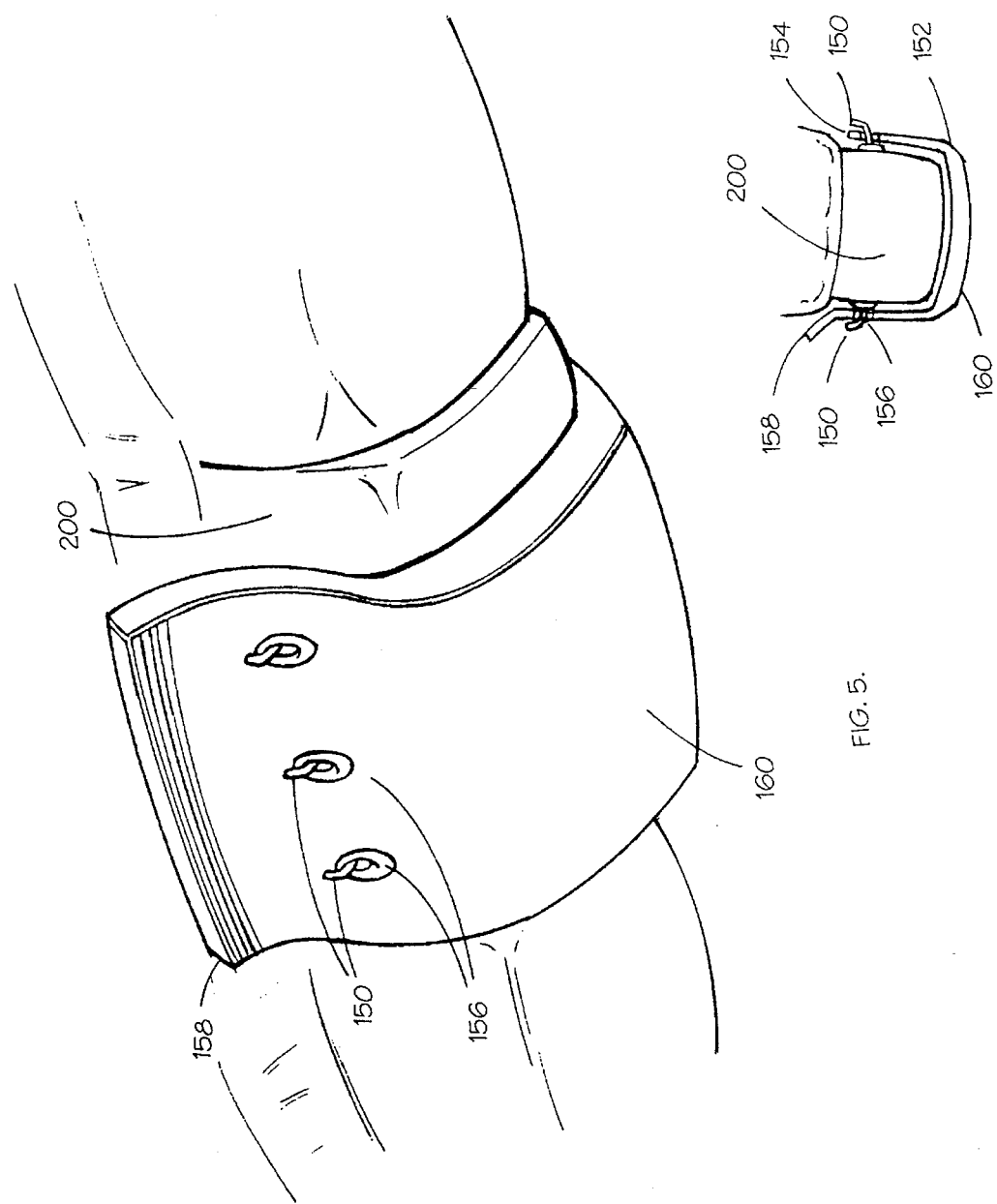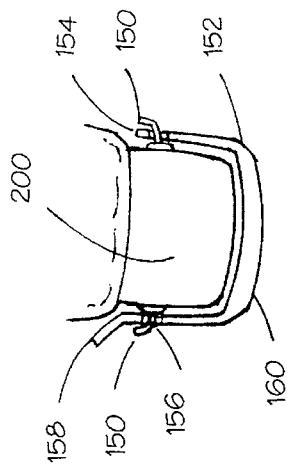

DEVICE FOR SENSING AND TREATING BRUXISM

FIELD OF THE INVENTION

This invention relates to bruxism and, more particularly, to a device for sensing and treating bruxism.

BACKGROUND OF THE INVENTION

Teeth are hard calcified structures attached to the upper and lower jaws of a human. Serving major functions such as chewing as well as providing for the formation of certain sounds by acting as a brace for the tongue, teeth can be divided into three general types: the incisors, the cuspids, and the molars.

The incisors, or front teeth are spade shaped which facilitate in the cutting of food. Central and lateral incisors are positioned in each quarter of the mouth followed by three cuspid teeth used in ripping of food. Two teeth in back of the cuspids are called the bi-cuspids each which have a cusp and are followed by first, second and third molars having a relatively flat chewing surface which permits the grinding or milling of food.

Teeth consist of an external portion, known as the crown, and a root that is embedded into the jaw. The outer layer of the crown is composed of a calcified tissue commonly known as enamel which overlays dentin which is a bone like substance extending from the inner surface of the enamel into the jaw to form the root. Covering the dentin of the root is a thin layer of hard tissue called cementum.

A problem with teeth that affects nearly all the population is tooth decay. Teeth are extremely suspectable to acidogenic bacteria which reacts with carbohydrates in the mouth to form acids capable of dissolving the enamel. The breakdown of the enamel permits other bacteria to penetrate the dentin eventually producing a cavity in the tooth.

One way of breaking down the enamel on the molars is from bruxism. Bruxism affects nearly fifteen percent of the population and commonly refers to teeth grinding which results in the physical destruction of the enamel leading to tooth decay as well as more serious problems. In advanced stages bruxism results in the abnormal and excessive grinding or clenching of teeth while an individual is asleep. In some instances a person may be so unaware of the problem that it may occur during waking hours. As the individual is usually not conscious of the problem, bruxism becomes a habit that is most difficult to treat.

The actual cause of bruxism is not clear and may be related to emotional stress or other psychological factors. A person with bruxism may be anxious, nervous or suppressing anger. Common treatments range from psychotherapy, sedatives, or tranquilizers and may further include biofeedback ranging from electrodes taped to the outside of the jaw to general relaxation techniques. Alternative methods of treatment are directed to breaking the habit and include the use of various tooth guard embodiments which may include alarming functions.

For instance, U.S. Pat. No. 5,277,203 discloses a tooth guard bite plate which is self-fitting. A problem with this device is that the guard physically covers the teeth making it an unsightly item suitable only for use in the home. More critical is the size of the device for it forms an improper fit and it may interfere with normal breathing. This may lead to additional problems such as inadequate oxygen to the brain. Should the guard become loose during sleep, the individual may choke or swallow the device.

U.S. Pat. No. 5,078,153 discloses a method and apparatus for sensing and treating teeth grinding through a tooth guard. A strip of piezo electric film is placed along a surface of the guard for use in conjunction with a miniaturized radio transmission which is inaudible to the human ear. A radio receiver amplifies the transmission to produce an audible tone or alarm which alerts the individual of bruxism. This invention utilizes an acrylic plastic formed from a custom plaster cast of an individual's teeth. This invention, as with the aforementioned invention, requires the use of a tooth guard that is acceptable during sleeping periods, but not acceptable in public. As with the previously mentioned tooth guard, even if the guard is fitted correctly, it can inhibit the breathing passageway.

U.S. Pat. No. 4,934,378 discloses yet another bruxism device. This device detects electrical signal impulses from electrodes located within an individual's ear and amplifies the signals to create an audible tone immediately indicating to the individual that bruxism is occurring. A benefit to this invention is that it may be worn during the day without distraction. Placement of the device in the ear may lessen the individual's ability to hear. Also the device cannot detect those who may clench their teeth without grinning them.

U.S. Pat. No. 5,190,051 discloses yet another device for treating bruxism. As with the aforementioned devices, it relies upon a mouth guard formed from a flexible tooth conforming U-shaped structure. This device further may lead to dislodgment which could cause harm should the device lodge in an individual's throat.

U.S. Pat. No. 4,304,227 discloses still another device for the treating of bruxism. This device sets forth an elaborate tooth guard that encompasses both the upper and lower jaw. This eliminates not only movement of the jaws but prevents breathing through the mouth forcing an individual to breath through the nose while the device is being worn. While this device would not allow dislodgment it does inhibit breathing as well as setting forth an unsightly device that would not be worn in public.

Thus, what is lacking in the art is a device that addresses the bruxism problem through use of an inconspicuous monitoring device that may be worn during the day or at night without discomfort to the individual and is secured in such a manner so as to prevent accidental dislodgment.

SUMMARY OF THE INVENTION

The instant invention is a method and device for sensing and treating bruxism. The apparatus has a universal shape allowing a single sized device to accommodate any size tooth. The preferred embodiment consists of an L-shaped rigid structure having a biting surface formed from a resilient compressible material such as rubber or plastic material having electrical elements in a normally open position for use in completing a circuit by touching of the elements forming a contact. The contact couples a power source and an audible alarm. The alarm indicates grinding or clamping of the teeth as completion of the circuit indicates that a form of bruxism is occurring.

The device is secured to a tooth by the use of clips bonded on an outer surface of a tooth and includes engagement tabs which are releasably secured to the bonded clips allowing an individual to install or remove the L-shaped structure as desired. Unlike conventional tooth guards of the prior art, the instant invention may be made less than the width of a tooth. Thus, the device fits within the confines of an individual's mouth without posing an aesthetic distraction. Therefore, if an individual chooses to wear the device during working hours, only the wearer will have knowledge of the device. If the individual is in a position for consuming food, removal can be inconspicuously performed.

The alarm means need not actually produce a sound as a vibration next to a tooth can be used to produce a resonant frequency capable of producing a sound in and of itself or creating such an annoyance that the individual is made aware of the situation. In addition, a time delay may be added to the circuitry so as to prevent an accidental alarm function from occurring if the jaws are closed only momentarily.

A second embodiment of the instant invention provides a bruxism guard which engages the aforementioned bonding clips and is used as a further step in treatment of bruxism and in those instances where an alarm function is not warranted or desired. When used by those individuals who have broken the cycle of bruxism, the guard operates as a reminder. Numerous instances exist where the habit of bruxism is not yet broken wherein an individual may choose not to have an alarm function operate such as in a romantic situation.

The instant invention may further be used for the sensing and treatment of snoring. The device operates in the same manner as the preferred embodiment having contact means which in this embodiment would be juxtapositioned at a spacial distance so as to detect a vibration from snoring so as to alert the individual of the problem. This is particularly advantageous in those situations where an individual may fall asleep while in public. For example, commuters often fall asleep on the way to or returning from work. In this situation, a person who may not have a problem with bruxism but does have a problem with snoring may insert the device and should snoring occur it would be immediately awakened by the audible alarm or tooth vibration so as not to create a spectacle or nuisance of himself in front of fellow passengers.

Alternatively, the device may be used by reversing of a time delay feature in which the device will signal sleep apnea in which an individual stops breathing for a period of time. In this embodiment should sleep apnea occur, the device will notice lack of vibration which will call the timer to operate. Should the lack of vibration, no breathing, occur for a period of say two minutes, the alarm function of the device is operate.

Thus, an objective of the instant invention is to disclose a concealable bruxism sensing apparatus that may be inconspicuously mounted inside the mouth of an individual without covering the front teeth or affecting their smile.

Yet another objective of the instant invention is to disclose a bruxism apparatus having an alarm juxtapositioned to the tooth for use in resonating a vibration against a tooth.

Still another objective of the instant invention is to teach the use of clips bonded to the side surface of a tooth allowing an individual to securely install the apparatus directly over the affected teeth allowing ease of removal but providing a secure attachment that will not inhibit the air passageway.

Still another objective of the instant invention is to disclose a bruxism guard which provides a cushion between the teeth to prevent bruxism when the use of an audible alarm is inappropriate.

Still another objective is to provide a device capable of sensing snoring and provide an alarm means to alert the individual of the problem, the alarm means including an optional timer circuit to prevent false readings.

Another objective is to provide a device capable of sensing sleep apnea by use of a timer circuit which operates after a period indicating lack of vibration.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1 is a perspective view of the instant invention with an exploded view of the two clips operatively associated with the device;

FIG. 2 is a pictorial side view of the instant invention attached to a tooth;

FIG. 3 is a perspective view of a tooth guard;

FIG. 4 is a pictorial view of a tooth guard of FIG. 3 attached to a tooth;

FIG. 5 is a pictorial view of a second embodiment of a tooth guard; and

FIG. 6 is a cross-section side view of FIG. 5.

DETAILED DESCRIPTION OF THE PREFERRED EMBODIMENT

Although the invention will be described in terms of specific embodiments, it will be readily apparent to those skilled in this art that various modifications, rearrangements and substitutions can be made without departing from the spirit of the invention. The scope of the invention is defined by the claims appended hereto.

Now referring to FIG. 1, set forth is a perspective view of the instant invention designated by numeral 10 formed from a horizontally disposed biting section 12 defined by an upper surface 14, a lower surface 16, a front edge 18 and opposing side edges 20 and 22. A mounting section 30 is defined by a vertically disposed mounting surface 32, formed perpendicular to the biting section 12, rear surface 34, top edge 36 and opposing side edges 38 and 40. Preferably the sections are formed from a single piece of plastic, rubber or the like non-metallic material which provides a shape retaining compressible support surface. Should an individual bite excessively on the material, the material will compress to prevent damage to the individual's teeth further completing an electrical contact. Each section may also be formed of separate pieces and joined along a common mating corner, the shape of the structure following the curvature of an individual's tooth. An upper portion of the mounting section 30 is formed outwardly from the otherwise vertical disposed mounting surface to avoid engagement with the gum line.

The biting section 12 includes spaced apart electrical elements 42 integrated into or secured thereto by use of a compressible material that allows a contact between the electrical elements when pressure is applied to the upper and lower surfaces 14 and 16, typical of an individual bruxism. The biting section 12 is positionable between opposing teeth by securing the device 10 to a single tooth by engaging clips 50 and 52. Embedded contacts providing a smooth surface which lessens bacteria growth.

Clip 50 is a one-piece inverted U-shaped holding device having a mounting segment 51, providing a surface for bonding to a tooth, and a frontal segment 54 spaced apart from the mounting segment in a biasing stance providing insertion chamber 56. The insertion chamber 56 is receptive to tab 60 which extends outwardly from side edge 38 of mounting section 30. Similarly, clip 52 includes mounting segment 62, providing a surface for bonding to a tooth, and a frontal segment 64 spaced apart from the mounting segment in a biasing stance providing insertion chamber section 66. The insertion chamber 66 is receptive to tab 70 extending outwardly from side edge 40. It is noted that tabs 60 and 70 may be formed of a single shank integrated through the mounting sections or molded into the structure further increasing rigidity of the segment. As noted with tab 70, a lower edge 72 leads to curved side wall 74 which allows for the engagement in insertion chambers 66 by forcing tab 64 outward providing positive engagement.

On the mounting section 30 of the device is located a battery 80 and an alarm mechanism 84. When a circuit is complete through element 42, the battery source 80 is electrically coupled to the alarm mechanism 84 providing a resonant sound or vibration indicating to the wearer that bruxism is occurring. An option includes the use of timer 84 to delay activation of the alarm mechanism 84, the delay prevents miscellaneous alarm signals should an individual accidently bite section 12. The timer will delay operation of the alarm for a period of time allowing the individual to remove pressure from the circuit to indicate lack of bruxism.

In addition, it should be noted that the circuit may be designed sensitive in which the circuit is completed by light vibrations such as snoring. Should the timer be placed in such a circuit and inverted, that is, operate only on lack of vibration, the device operates to treat sleep apnea.

FIG. 2 sets forth a pictorial view having a tooth 202 positioned on the upper jaw 204 with the device 10 secured to a side surface of the tooth by clip 50. The upper surface 14 of the device 10 is located beneath the tooth providing a biting surface between the tooth and teeth located on the lower jaw. The device may be inverted for use on the lower jaw although the results remain the same.

Now referring to FIGS. 3 & 4, set forth is a bruxism apparatus for use in those instances where an audible alarm is not necessary or desirable. In this embodiment the apparatus is formed from a single piece of rigid material formed into an L-shaped structure having a mounting section 100 and a biting section 102 with a frontal surface 104 and a rear surface 106, lower edge 108, upper edge 110, and side edges 112 and 114. The mounting section 100 includes a centrally disposed aperture 116 which allows for placement around a clip 50 bonded to a tooth 200 in instances where more than one anti-bruxism device has been attached. The embodiment shown encompasses two teeth with tabs 118 and 120 extending outwardly from side edges 112 and 114 allowing for attachment to mounting clips. In this manner an individual has the ability to customize a particular setting to encompass a plurality of teeth with the ability to alternate between alarming and non-alarming devices as necessary. The construction of the device, preferably made out of a resilient type plastic or rubberized material, provides sufficient cushion between the teeth to prevent teeth grinding. Preferably the alarming device is used to alert the individual when bruxism is occurring. The non-alarming embodiment is used once the individual has broken the habit of bruxism. The cushion operates as a positive reinforcement by providing a cushion that interrupts accidental biting and, due to the cushion size, can be felt by the individual when accidental bruxism occurs.

Now referring to FIGS. 5 and 6 set forth is yet another embodiment of the instant invention wherein hooks 150 are bonded to each side edge of a tooth 200. A flexible cushion 152 having a plurality of apertures located along a first end 154 and a plurality of apertures 156 located along second end 158 which are engagable with hooks 150 located on the opposite side of the tooth 200. The device may be constructed from a flexible plastic or rubberized material having the ability to wrap around the tooth or pre-formed in a shape therefore with an elongated portion of second end 158 allowing an individual to grasp the edge of the device for removal from the tooth by simply pulling on the edge allowing the apertures 156 to overcome hooks 150 for release of the device. It is noted that a center section 160 of the device is of a width so as to provide additional cushion to the tooth in an effort to prevent excess grinding of the tooth. The electrical components used to detect bruxism or modified to detect snoring or sleep apnea, may be placed within the center section providing an alternative tooth attachment method.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What I claim is:

1. An anti-bruxism device comprising: an L-shaped support means defined by a substantially vertical mounting section and a substantially horizontal biting section, said support means having a width and a length with an inner surface and an outer surface defining a thickness therebetween; and a mounting means bonded to at least one tooth for releasably securing said support means to a tooth side surface positioning said inner and outer surfaces of said biting section between the biting surfaces of teeth and said inner surface of said vertical section positioned along an outer surface of a tooth.

2. The anti-bruxism device according to claim 1 wherein said support means is a one-piece structure constructed from resilient compressible material.

3. The anti-bruxism device according to claim 2 wherein said compressible material is plastic.

4. The anti-bruxism device according to claim 2 wherein said compressible material is rubber.

5. The anti-bruxism device according to claim 1 including a bruxism sensing mechanism is defined by a contact means located in said biting section, an alarm means electrically coupled to said contact means, and a battery means electrically coupled to said contact means and said alarm means.

6. The anti-bruxism device according to claim 5 wherein said alarm means includes a timer mechanism.

7. A tooth protecting device comprising: an L-shaped support means defined by a vertical mounting section and a substantially horizontal biting section, said support means having a width and a length with an inner surface and an outer surface forming a thickness therebetween positionable between the biting surfaces of a tooth and said inner surface of said vertical section positioned along an outer surface of a tooth; contact means located in said biting section; alarm means electrically coupled to said contact means; battery means electrically coupled to said contact means; and a mounting means bonded to at least one tooth for releasably securing said support means to a tooth side surface.

8. The device according to claim 7 wherein said contact means is a first electrical element disposed in said biting section adjacent said upper surface spaced apart from a second electrical element disposed in said biting section adjacent said lower surface, said first and second element providing an electrical contact when touching each other.

9. The device according to claim 7 wherein said mounting means for releasably securing said support means to a tooth side surface is further defined as U-shaped clips bonded to a tooth side surface, each said clip having a mounting tab and a biasing tab forming a receptacle therebetween operatively associated with said support means.

10. The device according to claim 7 wherein said support means includes a first and second outwardly extending mounting tab for releasably engaging said mounting means.

11. The according to claim 7 wherein said support means is constructed from a resilient compressible material.

12. The device according to claim 11 wherein said resilient compressible material is plastic.

13. The device according to claim 11 wherein said resilient compressible material is rubber.

14. The device according to claim 7 wherein said vertical mounting section has a width equal to a width of said biting section, the width of said vertical mounting section less than the width of two adjacent human teeth.

15. The anti-bruxism device according to claim 7 wherein said alarm means includes a timer mechanism that delays operating said alarm means for a period of time to indicate a period of bruxism.

16. The anti-bruxism device according to claim 7 wherein said alarm means includes a timer mechanism that operates continuously and is turned off by said contact means to indicate sleep apnea.

17. The anti-bruxism device according to claim 7 wherein said contact means is vibration sensitive to detect snoring.

* * * * *